(12) United States Patent
Gopi et al.

(10) Patent No.: US 11,123,396 B2
(45) Date of Patent: Sep. 21, 2021

(54) FORMULATION FOR IMPROVING PHYSICAL ENDURANCE IN ATHLETES

(71) Applicant: Aurea Biolabs Private Limited, Cochin (IN)

(72) Inventors: Sreeraj Gopi, Cochin (IN); Karthik Varma Ayiranazhi Covilakam, Cochin (IN); Joby Jacob, Cochin (IN)

(73) Assignee: Aurea Biolabs Private Limited, Kolenchery (IN)

(*) Notice: Subject to any disclaimer, the term of this patent is extended or adjusted under 35 U.S.C. 154(b) by 0 days.

(21) Appl. No.: 16/312,167

(22) PCT Filed: Aug. 19, 2017

(86) PCT No.: PCT/IB2017/055026
§ 371 (c)(1),
(2) Date: Dec. 20, 2018

(87) PCT Pub. No.: WO2018/033892
PCT Pub. Date: Feb. 22, 2018

(65) Prior Publication Data
US 2019/0240280 A1 Aug. 8, 2019

(30) Foreign Application Priority Data
Aug. 19, 2016 (IN) .............................. 201641028194

(51) Int. Cl.
*A61K 36/906* (2006.01)
*A61K 36/31* (2006.01)
*A61K 36/736* (2006.01)
*A61K 36/185* (2006.01)

(52) U.S. Cl.
CPC .......... *A61K 36/906* (2013.01); *A61K 36/185* (2013.01); *A61K 36/31* (2013.01); *A61K 36/736* (2013.01); *A61K 2236/15* (2013.01); *A61K 2236/33* (2013.01)

(58) Field of Classification Search
None
See application file for complete search history.

(56) References Cited

U.S. PATENT DOCUMENTS 8,541,383 B2 * 9/2013 Gokaraju ............... A61K 8/602
424/725
2015/0190452 A1 * 7/2015 Hwang ................... A61K 31/35
424/756

FOREIGN PATENT DOCUMENTS

IN 2015 CH00541 * 8/2016

OTHER PUBLICATIONS

Azhar, M. et al. Pharmacologically Active Cardioprotective Plants at a Glance. Hamdard Medicus 58(1)51-83, 2015. (Year: 2015).*

Gopi S. et al. A Study on the Nitric Oxide Enhancing Ability of a Natural Phytochemical Formulation. Asian J of Pharmaceutical Technology and Innovation 4(16)1-6, 2016. (Year: 2016).*
Azhar, Misbahuddin, Nighat Anjum, and Neelam Quddusi. "Pharmacologically Active Cardioprotective Plants at a Glance." Hamdard Medicus 58.1. (2015). pp. 51-83.
HG/478; ukramt"kva°ik; Bhrata BhaiajyaRatnkara; Knowledge since 200 years (Source:www.tkdl.res.in). Accessed on Mar. 26, 2019. pp. 1-4.
Ismail, Tariq, Piero Sestili, and Saeed Akhtar. "Pomegranate peel and fruit extracts: a review of potential anti-inflammatory and anti-infective effects." Journal of Ethnopharmacology 143.2. (Sep. 28, 2012). pp. 397-405.
Jones, Andrew M. "Dietary nitrate supplementation and exercise performance." Sports medicine 44.1. (May 3, 2014). pp. 35-45.
Malaguti, Marco, Cristina Angeloni, and Silvana Hrelia. "Polyphenols in exercise performance and prevention of exercise-induced muscle damage." Oxidative medicine and cellular longevity 2013. (Jul. 2, 2013). pp. 1-10.
PCT International Search Report and Written Opinion of International Searching Authority dated Nov. 16, 2017, corresponding to PCT International Application No. PCT/IB2017/055026 filed Aug. 19, 2017.
SR06/90; Murungai Karpam; TherayarKappiyaml;Knowledge since 500 year (Source:www.tkdl.res.in). Accessed on Mar. 26, 2019. pp. 1-2.
Saokaew, Surasak, et al. "Clinical Effects of Krachaidum (*Kaempferia parviflora*): A Systematic review." Journal of Evidence-Based Complementary & Alternative Medicine, vol. 22.3. (Sep. 30, 2016). pp. 413-428.
Wattanathorn, Jintanaporn, et al. "Positive Modulation Effect of 8-week consumption of *Kaempferia parviflora* on Health-Related Physical Fitness and Oxidative Status in Healthy Elderly Volunteers." Evidence-Based Complementary and Alternative Medicine 2012 (2012). pp. 1-7.
Lamou, Bonoy, et al. "Antioxidant and Antifatigue Properties of the Aqueous Extract of Moringa oleifera in Rats Subjected to Forced Swimming Endurance Test." Oxidative Medicine and Cellular Longevity 2016 (2016). (pp. 1-10).
Trexler, Eric T., et al. "Effects of Pomegranate Extract on Blood Flow and Running Time to Exhaustion." Applied Physiology, Nutrition, and Metabolism 39.9 (Sep. 2014). pp. 1038-1042.
Gopi, Sreeraj, et al. "Natural sports supplement formulation for physical endurance: a randomized, double-blind, placebo-controlled study." Sport Sciences for Health 13.1 (Feb. 2017). pp. 1-13.
European Search Report for European Patent Application No. EP 17 84 1194 dated Feb. 13, 2020.

* cited by examiner

*Primary Examiner* — Ralph J Gitomer
(74) *Attorney, Agent, or Firm* — Lempia Summerfield Katz LLC

(57) ABSTRACT

The present disclosure discloses a herbal formulation in powdered dosage form, which is useful to enhance the physical endurance or strength in athletes. The disclosure also includes a method of preparation of the formulation, which involves the encapsulation of the natural ingredients in a natural matrix. The formulation comprises *Moringa oleifera, Kaempferia parviflora* and *Punica granatum* that are processed to obtain the product in powder form by encapsulation of the natural ingredients in a natural matrix. The formulation increased the nitrate and nitrite levels in serum and saliva in human and is useful to improve the general health of the athletes.

4 Claims, 6 Drawing Sheets

| Sr.No | Ingredients | Composition (%) |
|-------|-------------|-----------------|
| 1 | *Moringa oleifera* leaf extract | 45%-50% |
| 2 | *Kaempferia parviflora* extract | 12%-15% |
| 3 | *Punica granatum* polyphenols | 32%-35% |

|  | Placebo (U/L) | | Supplement (U/L) | |
| --- | --- | --- | --- | --- |
|  | Pre-Exercise | Post-Exercise | Pre-Exercise | Post-Exercise |
| Day 0 | 623.6 ± 151.4 | 673.7 ± 168.3 | 527.8 ± 47.5 | 578.08 ± 118.8 |
| Day 22 | 653.6 ± 160.2 | 635.0 ± 158.7 | 608.0 ± 114.9 | 582.5 ± 114.1 |

FIGURE 8

| Group | Day 0 (nmol/mL) | Day 22 (nmol/mL) | % of Changes | P Value |
| --- | --- | --- | --- | --- |
| Supplement | 14.6 ± 1.1 | 9.9 ± 2.2 | 47.47 | 0.008 |
| Placebo | 14.1 ± 1.3 | 14.2 ± 1.2 | 0.7 | 0.521 |

FIGURE 9

| Group | Day 0 (μg/24h) | Day 22 (μg/24h) | % of Changes | P Value |
| --- | --- | --- | --- | --- |
| Supplement | 225.1 ± 91.1 | 354.3 ± 80.9 | 36.47 | 0.045 |
| Placebo | 154 ± 91.3 | 155.6 ± 121.6 | 1.03 | 0.39 |

FIGURE 10

FORMULATION FOR IMPROVING PHYSICAL ENDURANCE IN ATHLETES

CROSS-REFERENCE TO RELATED APPLICATION

The present patent document is a § 371 nationalization of PCT Application Ser. No. PCT/IB2017/055,026, filed Aug. 19, 2017, designating the United States, which is hereby incorporated by reference, and this patent document also claims the benefit of Indian Application No. 201641028194, filed Aug. 19, 2016, which is also hereby incorporated by reference.

TECHNICAL FIELD OF THE DISCLOSURE

The present disclosure discloses an herbal formulation comprising Methoxy flavones obtained from *Kaempferia parviflora* (black ginger), saponins from *Moringa oleifera* and polyphenols from *Punica granatum* (pomegranate) in a powdered dosage form, which is useful to enhance the physical endurance or strength in athletes. The disclosure also describes a method of preparing the formulation by encapsulation of the natural ingredients in a natural matrix.

BACKGROUND

Physical endurance is a state of health and more precisely provides the foundation for performing the activities of daily living and protection against disease conditions and is the basic criteria for participation in sports.

Physical strength or endurance is of utmost importance for athletes as it helps in optimizing performance in a certain sport. Each sport requires strength for optimal performance, without which it is not possible to perform on the field continuously. Physical fitness and skill are equally important traits that an athlete requires and therefore an athlete has to work constantly towards developing both at the same time.

There are various chemicals in the body, which are responsible for fitness such as nitric oxide (NO), Erythropoietin (EPO), Monoamine oxidase (MAO-B) etc. NO is an endothelium-derived relaxing factor, which functions as a cell-signaling factor in both physiological and pathological process. NO also plays a crucial role because of its vasodilation activity in blood vessels as it helps in maintaining the fluid homeostasis and in regulating the blood pressure. NO in blood is a major contributor in achieving maximum performance during exercise.

EPO is associated with production of red blood cells and acts as a marker for blood oxygenation and iron availability. MAO-B prevents the breakdown of dopamine. Anti-oxidants also play a crucial role in maintaining the performance of the athletes by preventing breakdown of NO.

The U.S. Pat. No. 8,603,546 titled "Herbal supplement for increased muscle strength and endurance for athletes" discloses a composition comprising whole plant extract of *Leucojum aestivum* comprising galanthamine as an active ingredient to an athlete before and during sports activities to enhance the performance. However, the composition may not be effective in improving the physical endurance in athletes.

The U.S. Pat. No. 6,051,236 titled "Composition for optimizing muscle performance during exercise" discloses a nutritional composition in a dry powder form for optimizing muscle performance during exercise and for enhancing muscle cell repair and recovery following the cessation of exercise, containing carbohydrates, proteins, vitamins and amino acids. This formulation does not disclose use of herbal plants to improve the physical fitness of athletes.

The US application number US20010041187 titled "Performance-enhancing dietary supplement" discloses a dietary supplement for enhancing physical performance of human, which includes a soy protein isolate, free form amino acids, medium chain triglycerides, creatine monohydrate, l-carnitine, grape seed extract, coenzyme Q10, *Piper nigrum* extract, and alpha lipoic acid. This formulation lacks effectiveness with respect to improvement of the physical fitness of athletes.

The US application number US20140205687 titled "*Tribulus terrestris, Avena sativa* and *Panax ginseng* extract combination" discloses a herbal pharmaceutical product obtained from *Tribulus terrestris, Avena sativa* and *Panax ginseng* plants, which is used as a supplement and support to increase muscle strength, body stamina and physical performance and is also used to treat cardiovascular diseases. The claimed invention does not disclose the method of preparation of herbal composition.

One of the major factors that help athletes to achieve high level performance in sports is by improving the strength, speed and endurance of physical performance. Hence, there is a need for a non-toxic and a cost effective preparation, preferably the herbal formulation containing combination of different plant extracts that helps in improving physical performance.

SUMMARY

The disclosure discloses the herbal formulation comprising methoxy flavones obtained from *Kaempferia parviflora* (black ginger), saponins from *Moringa oleifera* and polyphenols from *Punica granatum* (pomegranate) in a powdered dosage form to enhance the physical endurance in athletes. The disclosure further describes a method of preparing the formulation by encapsulation of the natural ingredients in a natural matrix.

The herbal composition comprises *Kaempferia parviflora* extract at the concentration in the range of 12%-15% w/w, *Moringa oleifera* leaf extract at the concentration in the range of 45%-50% w/w and *Punica granatum* (pomegranate) extract at the concentration in the range of 32%-35% w/w.

The disclosure further discloses a method of preparation of the formulation. The method involves the steps of crushing *Moringa oleifera* leaf to obtain its powder and extracting the active constituents using hydro alcohol, crushing *Kaempferia parviflora* raw material to obtain the powder and the active constituent 5, 7 dimethoxy flavone is extracted using ethanol. Further, *Kaempferia parviflora* extract and *Moringa oleifera* extract are mixed together to form a uniform mixture and the dried peel of *Punica granatum* is crushed and the active constituent punicalagin is extracted using water and further spray dried to obtain its powder. *Punica granatum* dried peel extract is mixed with uniform mixture of *Kaempferia parviflora* extract and *Moringa oleifera* extract. The uniform mixture of all the three extracts namely *Punica granatum* dried peel extract, *Kaempferia parviflora* extract and *Moringa oleifera* extract are blended and homogenized to obtain a uniform matrix. Finally, the uniform matrix is subjected to spray drying to obtain the final product in the powder form for use.

The formulation is effective in increasing the nitrate and nitrite levels in serum and saliva in human and also improved the pharmacokinetic parameters. The formulation is effective in improving the physical endurance in athletes.

BRIEF DESCRIPTION OF DRAWINGS

FIG. 2(*b*) illustrates the structure of niazirin, which is other constituent of *Moringa oleifera*.

FIG. 8 illustrates the levels of pre-exercise and post-exercise lactate dehydrogenase in the supplement and placebo group.

FIG. 9 illustrates the levels of pre-exercise and post-exercise malondialdehyde in the supplement and placebo group.

FIG. 10 illustrates the levels of pre-exercise and post-exercise dopamine in the supplement and placebo group.

DETAILED DESCRIPTION

The present disclosure discloses an herbal formulation, which is obtained from different plant extracts that helps in improving the general health, strength and also the stamina of athletes to perform the activities. The disclosure also discloses a method of preparing the formulation by encapsulation of the natural ingredients in a natural matrix.

Figure 1:
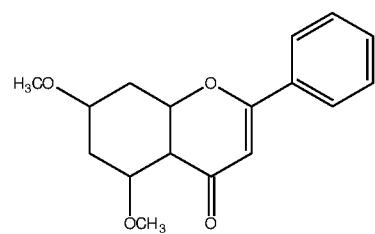
FIG. 1 illustrates the structure of methoxyflavone, which is a flavanoid constituent present in *Kaempferia parviflora*.

FIG. 1 illustrates the structure of methoxy flavone. Methoxy flavone is a flavanoid present in *Kaempferia parviflora*. 5, 7 dimethoxy flavone is a major constituent in *Kaempferia parviflora* that increases the nitric oxide levels in the human body. 5, 7 dimethoxy flavone also inhibit the activity of phopsphodiesterase (PDE5) and is used for treating metabolic ailments and it is also an aphrodisiac compound and physical activity enhancer.

Figure 2:
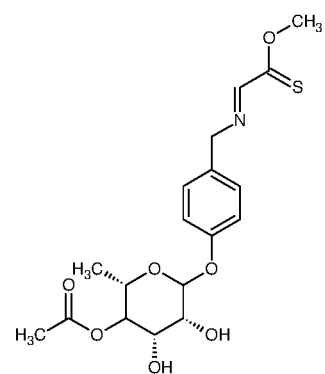
FIG. 2(*a*) illustrates the structure of niazimin A, which is one of the constituent present in a *Moringa oleifera*.
Figure 2:
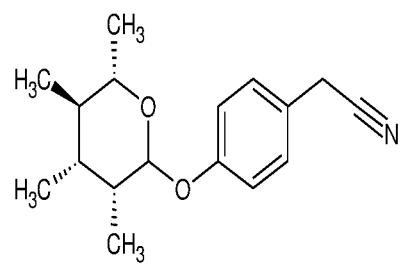

FIG. 2(*a*) illustrates the structure of niazimin A and FIG. 2(*b*) illustrates the structure of niazirin. Niazimin A and niazirin are active constituents present in *Moringa oleifera*. The extract obtained from the leaf of *Moringa oleifera* stimulates the nitric oxide levels in the human body. The active components inhibit the PDE5 activity and improve vasodilation process. The leaf extract also prevents the breakdown of dopamine by inhibition of MAO-B activity. It also acts as a source of nutrition and natural energy booster, lowers blood pressure and also exhibits detoxifying activity.

Figures 3, 4:
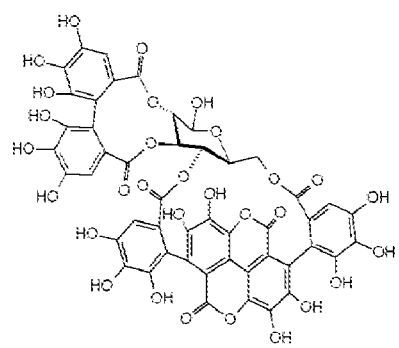
FIG. 3 illustrates the structure of punicalagin, which is a polyphenol.
FIG. 4 illustrates the preferred composition of the formulation to improve physical endurance.

FIG. 3 illustrates the structure of punicalagin. The husk and peels of pomegranate comprises 26% to 30% of total fruit weight and higher amount of phenolic compounds than in the fruit pulp. Punicalagin is a polyphenol present in pomegranate, which exhibits antioxidant activity. The pomegranate polyphenols prevents the breakdown of nitric oxide in the human body.

FIG. 4 illustrates the composition of the formulation to improve the physical endurance. The herbal composition for the improvement of physical endurance of the disclosure comprises of flavanones obtained from *Kaempferia parviflora* extract at the concentration in the range of 12%-15% w/w, saponins from *Moringa oleifera* leaf extract at the concentration in the range of 45%-50% w/w and polyphenols from *Punica granatum* (pomegranate) extract at the concentration in the range of 32%-35% w/w.

Figure 5:
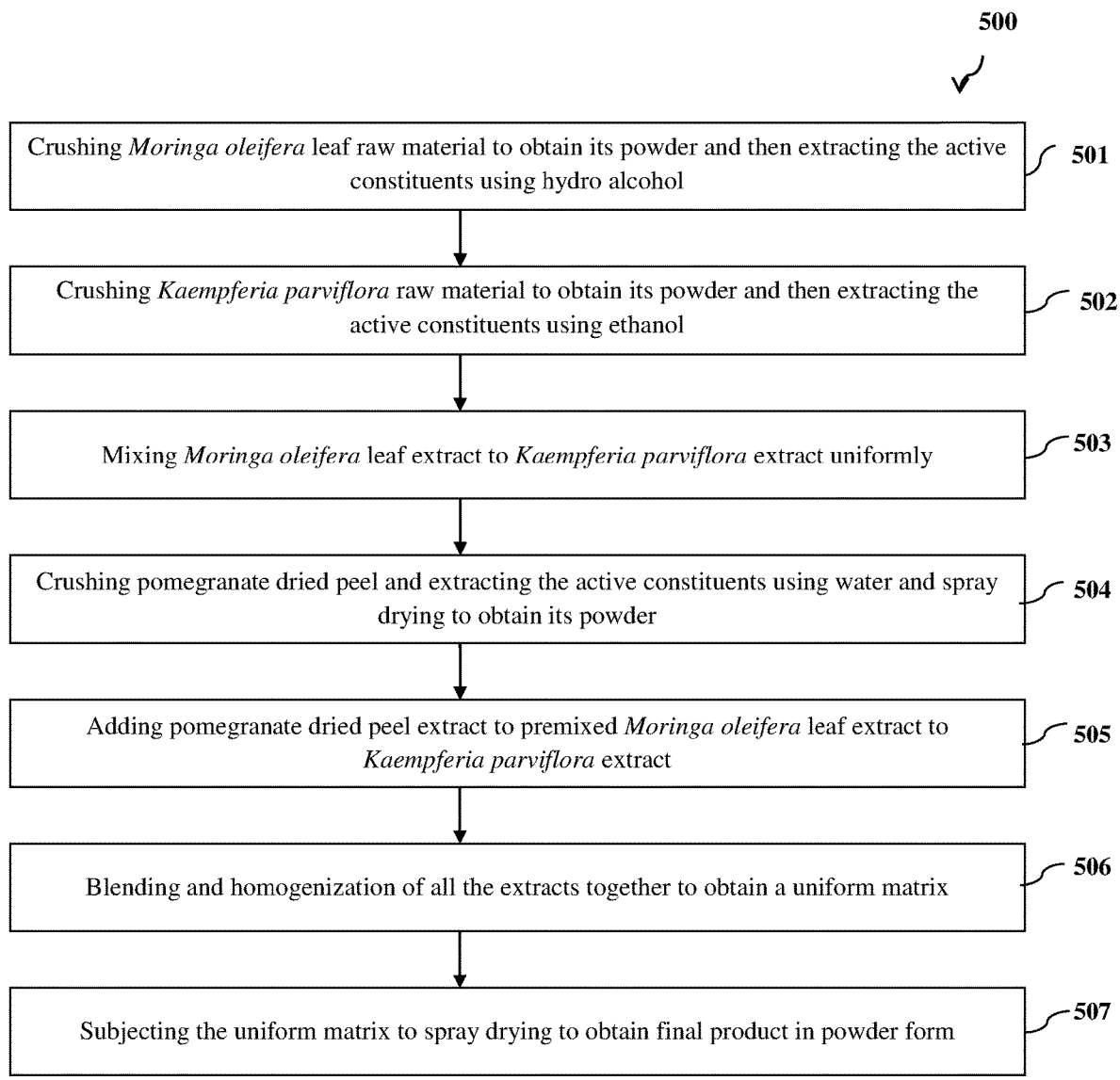
FIG. 5 illustrates a flow chart for a method for preparation of the composition.

FIG. 5 illustrates a flow chart of the method for preparation of the composition. The method (500) starts with crushing of *Moringa oleifera* leaf to obtain its powder and extracting the active constituents namely niazimin A and niazirin using hydro alcohol (501). At step (502), *Kaempferia parviflora* raw material is crushed to obtain the powder and the active constituent 5, 7 dimethoxy flavones is extracted using ethanol. At step (503), *Kaempferia parviflora* extract and *Moringa oleifera* extract are mixed together to form a uniform mixture. At step (504), dried peel of *Punica granatum* is crushed and the active constituent punicalagin is extracted using water and further spray dried to obtain its powder. At step (505), *Punica granatum* dried peel extract is mixed with uniform mixture of *Kaempferia parviflora* extract and *Moringa oleifera* extract. At step (506), the uniform mixture of all the three extracts namely *Punica granatum* dried peel extract, *Kaempferia parviflora* extract and *Moringa oleifera* extract are further blended and homogenized to obtain a uniform matrix. The final step (507) comprises of spray drying of the uniform matrix of all the three herbal extracts and the final product is available in the powder form for use.

In order that this invention to be more fully understood the following preparative and testing example is set forth. The example is for the purpose of illustration only and is not to be construed as limiting the scope of the invention in any way.

Example 1: The Efficacy of the Formulation in Humans

The formulation is tested for its activity in healthy human volunteers. The volunteers are administered with the formulation at the concentration of 250 mg referred as supplement group and the volunteers without formulation referred as placebo group. The parameters such as pharmacokinetics and levels of nitrate, nitrite, lactate dehydrogenase, malondialdehyde and dopamine are evaluated in serum and saliva. The results show that the administration of the formulation increased the levels of nitrate in serum and saliva. The levels of nitrite also increased in serum and saliva after administration of the formulation without inducing any toxicity. The formulation further increased the level of dopamine, decreased lactate dehydrogenase and malondialdehyde levels after exercise.

Figure 6A:
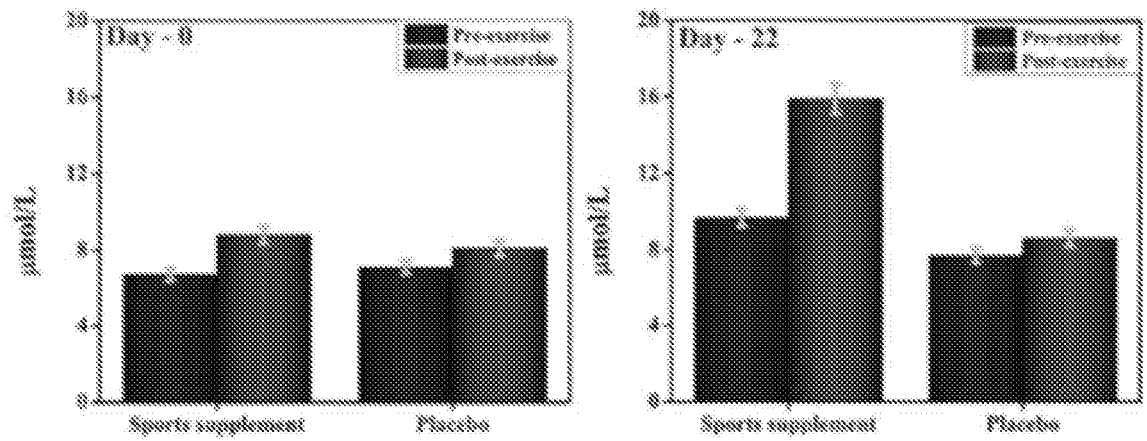
FIG. 6*a* illustrates pre-exercise and post-exercise increase in serum nitrate level in human.
Figure 6B:
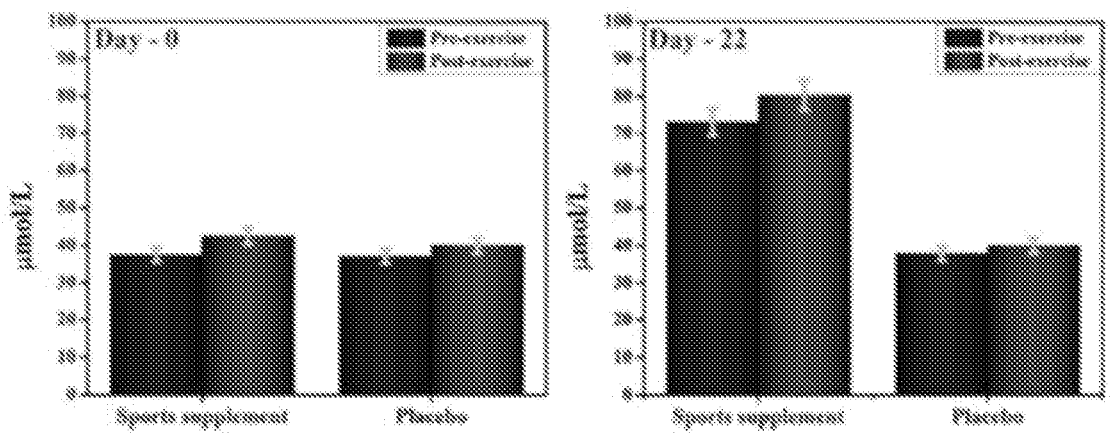
FIG. 6*b* illustrates pre-exercise and post-exercise increase in saliva nitrate level in human.

FIG. 6 illustrates the pre-exercise and post-exercise nitrate level in serum and saliva in supplement group and placebo group. The administration of the formulation increased nitrate level in serum and plasma in supplement group. FIG. 6*a* illustrates pre-exercise and post-exercise increase in serum nitrate level in supplement group. FIG. 6*b* illustrates pre-exercise and post-exercise increase in saliva nitrate level in supplement group. The serum nitrate increased from 6.7 μmol/L (day 0) to 9.7 μmol/L (day 22) and the increment is 31% before exercise. Similarly, there is 45% increase in serum nitrate after exercise and it is elevated from 8.8 μmol/L to 15.9 μmol/L.

Figure 7A:
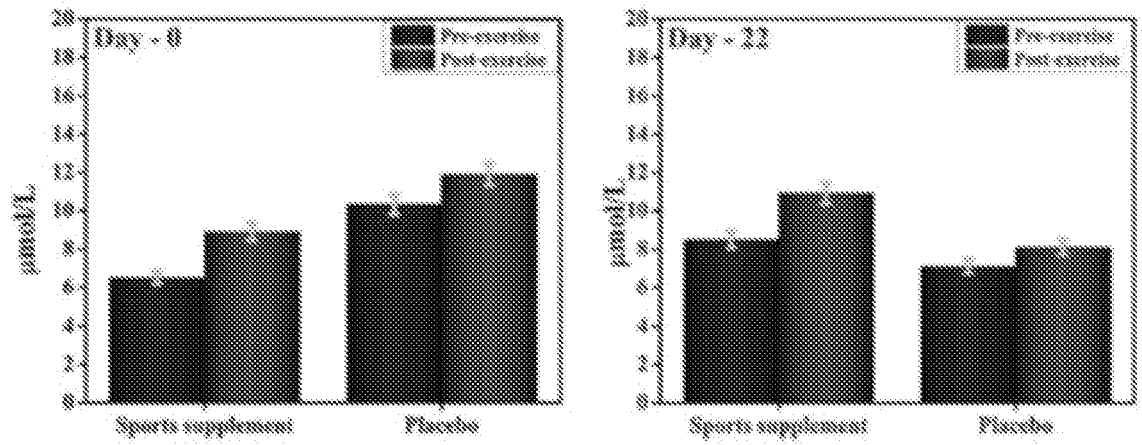
FIG. 7*a* illustrates pre-exercise and post-exercise increase in serum nitrite level in human.
Figure 7B:
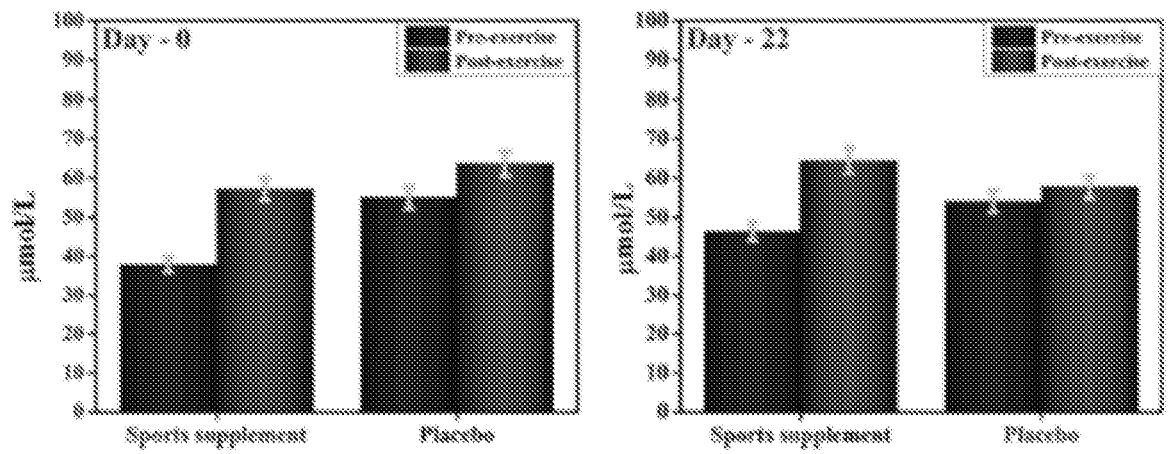
FIG. 7*b* illustrates pre-exercise and post-exercise increase in saliva nitrite level in human.

FIG. 7 illustrates the pre-exercise and post-exercise nitrite level in serum and saliva in supplement group and placebo group. The administration of the formulation increased nitrite level in serum and saliva in supplement group. FIG. 7a illustrates pre-exercise and post-exercise increase in serum nitrite level in supplement group. FIG. 7b illustrates pre-exercise and post-exercise increase in saliva nitrite level in supplement group. The serum nitrite increased from 37.5 to 73.1 (μmol/L) and from 42.5 to 80.3 (μmol/L) for pre- and post-exercises, respectively. It is observed that is a remarkable rise in serum nitrite and 49% and 47% for pre- and post-exercises, respectively.

The maximum nitrate concentration achieved in saliva and serum within 1.58 and 1 h, respectively, show that in the acidic stomach, nitrate and nitrite are absorbed from the intestine to the circulation and converted to bioactive NO in blood and tissues under physiological hypoxia.

FIG. 8 illustrates the levels of pre-exercise and post-exercise lactate dehydrogenase in the supplement and placebo group. The results show that administration of the formulation decreased pre-exercise and post-exercise lactate dehydrogenase level. Serum inflammatory biomarker lactate dehydrogenase level decreased from 673.7 U/L to 578 U/L in the supplement group without significant change in placebo group.

FIG. 9 illustrates the levels of pre-exercise and post-exercise malondialdehyde in the supplement and placebo group. The results show that administration of the formulation decreased malondialdehyde level from 14.6 to 9.9 nmol/mL without significant change in placebo group.

The decrease in the oxidative stress markers lactate dehydrogenase and malondialdehyde indicates the reduction of oxidative stress after exercise in response to the administration of the formulation.

FIG. 10 illustrates the levels of pre-exercise and post-exercise dopamine in the supplement and placebo group. The results show that administration of the formulation increased the dopamine levels from 225.1 μg/24 h to 354.3 μg/24 h. The increase in post-exercise dopamine levels indicates the improvement of mental health and physical functioning in the supplement group.

The formulation of the invention is effective in increasing the serum and saliva levels of nitrate and nitrite in humans. The formulation also increased the pharmacokinetic parameters. The formulation is useful in improving the physical endurance in athletes. The formulation also helps to increase muscle strength, body stamina, physical performance, post-exercise muscle recovery and reduction of oxidative stress in muscles in athletes.

We claim:

1. A formulation for improving of physical endurance, the formulation comprising:
   a. Methoxy flavone extract from *Kaempferia parviflora* at a concentration in a range of 12%-15% w/w;
   b. Saponin rich leaf extract from *Moringa oleifera* at a concentration in a range of 45%-50% w/w; and
   c. Polyphenol rich extract from *Punica granatum* at a concentration in a range of 32%-35% w/w,
   and the extracts form a uniform matrix and are homogenized and spray dried thus forming an encapsulated powdered form of the formulation.

2. The formulation as claimed in claim 1, wherein *Kaempferia parviflora* comprises flavanones extracted using ethanol.

3. The formulation as claimed in claim 1, wherein *Moringa oleifera* leaf extract comprises saponins extracted using hydro alcohol.

4. The formulation as claimed in claim 1, wherein the formulation increases nitrate and nitrite levels in serum and saliva in human.

* * * * *